United States Patent
Persky

(10) Patent No.: US 7,457,443 B2
(45) Date of Patent: Nov. 25, 2008

(54) IMAGE GUIDED IMPLANTOLOGY METHODS

(75) Inventor: Nathan Persky, Mevasseret Zion (IL)

(73) Assignee: Image Navigation Ltd., Moshav Ora (IL)

( * ) Notice: Subject to any disclaimer, the term of this patent is extended or adjusted under 35 U.S.C. 154(b) by 644 days.

(21) Appl. No.: 10/480,948

(22) PCT Filed: May 30, 2002

(86) PCT No.: PCT/IL02/00421

§ 371 (c)(1),
(2), (4) Date: Jul. 26, 2004

(87) PCT Pub. No.: WO02/096261

PCT Pub. Date: Dec. 5, 2002

(65) Prior Publication Data

US 2005/0163342 A1    Jul. 28, 2005

Related U.S. Application Data

(60) Provisional application No. 60/294,227, filed on May 31, 2001.

(30) Foreign Application Priority Data

Feb. 6, 2002    (IL) .................................... 148070

(51) Int. Cl.
*G06K 9/00* (2006.01)

(52) U.S. Cl. ................. 382/128; 382/103; 128/922; 348/66; 433/29

(58) Field of Classification Search ................. 382/103, 382/128, 131, 132; 128/922; 348/66; 433/29
See application file for complete search history.

(56) References Cited

U.S. PATENT DOCUMENTS

| 4,325,373 A | 4/1982 | Slivenko et al. |
| 5,133,660 A | 7/1992 | Fenick |
| 5,343,391 A | 8/1994 | Mushabac |
| 5,383,454 A | 1/1995 | Bucholz |
| 5,688,118 A | 11/1997 | Hayka et al. |
| 5,842,858 A | 12/1998 | Truppe |
| 5,967,777 A | 10/1999 | Klein et al. |
| 6,076,008 A | 6/2000 | Bucholz |

(Continued)

FOREIGN PATENT DOCUMENTS

DE    198 30 449    1/2000

(Continued)

*Primary Examiner*—Aaron W Carter
(74) *Attorney, Agent, or Firm*—Husch Blackwell Sanders LLP

(57) ABSTRACT

A method for correcting inherent distortions in a CT or MRI imaging process, or distortions arising from excessive patient movement during the scan by means of a registration device inserted into the mouth of the patient at the time the scan is being performed. The registration device incorporates a set of fiducial markers disposed in a predetermined three-dimensional pattern. The exact positions of the fiducial markers are known with respect to each other, thus providing a three-dimensional reference against which the resulting images can be compared. Additionally, a method whereby three-dimensional CT or MRI images taken prior to an operation, are accurately registered and integrated with real-time tracking positional data of the patient's body part and instruments operating thereon. Application is described for the drilling of a patient's jaw for the placement of dental implants.

24 Claims, 5 Drawing Sheets

U.S. PATENT DOCUMENTS 6,228,089 B1  5/2001  Wahrburg
6,236,875 B1  5/2001  Bucholz et al.

FOREIGN PATENT DOCUMENTS

| EP | 0488987 | * | 1/1996 |
| EP | 0 955 565 | | 11/1999 |
| JP | 2001 027700 | | 1/2001 |
| WO | WO 02/096261 | | 12/2002 |

* cited by examiner

IMAGE GUIDED IMPLANTOLOGY METHODS

FIELD OF THE INVENTION

The present invention relates to the field of the correction of scanned images of an object and the relation of these images to the actual real-life position of the object, and especially as applied to CT images of a subject's teeth and the relation of these CT images to the actual teeth in the subject's jaw, as used in the preparation of drilled cores for the placement of dental implants.

BACKGROUND OF THE INVENTION

The use of threaded inserts, generally made of titanium, has become the dominant technology currently used for dental implant surgery. Such inserts must be precisely located in the tooth in order to provide optimum aesthetic and beneficial results. Bone preparation must be precise and should preferably be carried out with the implant site and shape in constant view of the dental surgeon. In particular, during the drilling phase of the bone preparation, great care must be taken to avoid causing injury to the patient. Examples of such potential damage include inadvertent entry into the mandibular nerve canal, possible perforation of the cortical plates, or damage to adjacent teeth.

In order to achieve these objectives, exact knowledge of the bone topology of the jaw must be on hand. Such information is today obtainable from computer-generated panoramic and oblique radiographic CT scans of the jaw, which provide the cross-sectional shape of the jaw at every point throughout the arch on a 1:1 scale. In order to use the information on such CT images optimally, the dental surgeon should be provided with a continuous, real-time, three-dimensional image of the location and direction of the drill during the drilling procedure into the bone at all times during its execution. As a result, there should be optimal correlation between the implantation planning and the actual surgical performance, and accurate placement of the insert, even by less experienced clinicians, and additionally, reduction to a minimum of any danger of damage to vital anatomical structures, such as the inferior alveolar nerve, the maxillary antrum, the nasal cavity, adjacent teeth, or cortical plates.

However, the successful and accurate implementation of a system providing such information is dependent on the accuracy of the initial input data of the CT imagery provided to the system computer. Such data as supplied by the CT scanner may generally be distorted, whether because of imperfections in the algorithms used in the scanner software, or because of interpolations made in areas where exact measurements are not performed, or simply because of inaccuracies due to excessive patient movement during the CT scan. Very high accuracy is required in dental implantology, where even a fraction of a millimeter of excess penetration or a degree or two of misalignment, can mean the difference between a successful procedure and an unsatisfactory one, or even between a safe procedure and injury to the patient. Consequently, the distortion inherent in generally available CT scans is such that such scans cannot be used as supplied, for accurate image-guided dental implantology.

There therefore exists a serious need for a method of compensating or correcting for such CT distortion for use in image-guided implantation surgery. In addition, such a method would also be applicable and necessary for use in other accurate, image-guided surgical or industrial procedures which utilize scanned image information for determining an exact overall picture of the imaged subject or object.

Furthermore, even if such accurately corrected CT imagery were available, it is necessary to relate the computer-generated virtual images of the patient's jaw with the actual teeth in the patient's jaw, and with the position of the dental surgeon's hand and drill. Thus, it is necessary to correlate a definite point on a CT scan with its matching point in the patient's jaw, and a stereometric angle on the scan with the corresponding angle in the patient's jaw. Without such correlation, even the most accurate and undistorted CT scan is of very limited use for guiding any sort of real time surgical procedure, such as implant preparation. Furthermore, the correlation must take into account and track any motion of the patient's jaw during the procedure. In U.S. Pat. No. 5,842,858 to M Truppe, for "Method of Imaging a Person's Jaw and a Model thereof", there is described a method whereby such correlation and tracking are performed using a 3-D sensor attached, for instance by means of screws, to the outside of the jaw of the patient, which is referenced by means of a tracking system to another 3-D sensor temporarily located inside the jaw. Such a referencing method may be considered disadvantageous since it entails subject involvement, and may also be dependent on operator skill in attachment of the 3-D sensor to the outside of the patient's jaw. Furthermore, physiological changes taking place in the tissue and muscle of the patient's jaw during the course of the procedure may induce inaccuracies in the position of the sensor. These factors may compromise the high accuracy required for an accurate implant procedure.

There therefore exists a serious need for a method of correlating virtual CT images previously obtained of a patient's jaw with the actual situation being followed by the drill in real time in the patient's jaw during a dental surgical procedure. The method should ideally be performed with minimal interaction with the patient's jaw, in order to reduce subjective inaccuracies as much as possible. Furthermore, it should be simple enough to be executable by personnel other than the dental surgeon himself, such as a dental technician. It is to be understood that such a method would also be useful and applicable in other accurate, image-guided surgical or industrial procedures which utilize scanned image information for determining the overall picture of a real-time procedure being performed.

The disclosures of all publications mentioned in this section and in the other sections of the specification, are hereby incorporated by reference, each in its entirety.

SUMMARY OF THE INVENTION

The present invention seeks to provide new methods for ensuring the accurate use of CT or MRI scanned images in surgical procedures, such as image-guided implantology. There is thus provided according to a first preferred embodiment of the present invention, a method whereby inherent distortions in the CT or MRI imaging process, or distortions arising from excessive patient movement during the scan are corrected by means of a registration device inserted into the mouth of the patient at the time the scan is being performed. To this registration device is attached in a reproducible manner, a device known as a distortion body which contains a set of fiducial markers disposed in a predetermined three-dimensional pattern, and whose location is registered on the images during the scanning. The exact positions of the fiducial markers are known with respect to each other, thus providing a three-dimensional reference against which the resulting images can be compared. This provides accurate spatial position information for correcting any distortion present in the scanning and image-processing procedure. Calculations are then performed for determining the exact location of the fiducials in the CT data, the distortion between the three dimensional image obtained and the known true location of the fiducials, and for producing a correction function for use in interpreting the CT or MRI data such that it provides accurate positional data.

There is also provided according to another preferred embodiment of the present invention, a method whereby the three-dimensional, pre-operative CT or MRI images are accurately registered and integrated with the real-time intra-operative tracking positional data. The latter are defined by two characteristic activities. Firstly, the position and orientation of the drill is supplied to the system, preferably by means of LED's attached to the drill body. The position of these LED's is preferably tracked by means of a triangulation tracking and measurement technique, or any other suitable tracking and measurement technique, such that the drill's spatial position and orientation is known at all times. Secondly, the position of the tooth being drilled in the patient's jaw is tracked preferably by means of a reference tracking body the position of which is defined relative to the patient's jaw. The reference tracking body preferably incorporates a set of LED's, which are tracked by the tracking system. Thus, the real-world positions both of the drill and of the tooth can be spatially and definitively tracked by the system.

These images are then spatially and angularly related to the pre-operative images by means of a pre-registration procedure performed according to another preferred embodiment of the present invention, in which a registration body containing fiduciary markers is inserted in a predefined manner into a registration jig, prior to commencement of any work on the patient. The position of the jig together with the inserted registration body is tracked by the tracking system preferably by means of LED's mounted on the jig. Alternatively and preferably, the position of the registration body can be made known to the tracking system by any other suitable positional determining device, such as by a manually held stylus which is touched onto a reference point of the registration body, or even onto the fiducial markers themselves. Since the fiducial markers are the same ones as were incorporated in the scans previously made with the registration body in the patient's mouth, and thus bear a predefined and fixed spatial and angular relationship to the registration body, and the registration body to the patient's teeth, this correlation enables the virtual-world CT scans to be related to the functional world of the tooth and drill as tracked in real time by the system. Since this registration procedure is performed outside of the patient's mouth, it has a number of advantages over prior art registration procedures performed involving the patient's jaw. In the first place, since the registration procedure is performed outside of the patient's mouth, and without patient involvement, the accuracy and the reliability of the registration process is increased, as is the patient comfort level, for the reasons stated hereinabove. Secondly, the registration process can be performed at any time before the procedure on the patient, and requires less skill and time than an intra-oral registration procedure, as in the prior art, with all the advantages thereby engendered.

The term registration device as used and claimed throughout this application, is understood to include any form of device operative for acquiring positional determination data of the object to be imaged. Likewise, the term reference tracking body as used and claimed throughout this application, is understood to include any form of sensor device operative for providing 3-D information about the position of the tracked body.

There is also provided in accordance with another preferred embodiment of the present invention, a a method of compensating for distortions generated in an imaging process, comprising the steps of (a) providing a registration device with a plurality of markers disposed in a predetermined three-dimensional pattern, the markers being rendered visible in the imaging process, (b) producing a scanned image of an object of interest in the presence of the registration device, and (c) correcting the data of the scanned image such that the image of the markers accurately reproduces the predetermined three-dimensional pattern. The plurality of markers are preferably disposed either within the registration device, or within a body attached to the registration device. The above-described method can preferably be used for computerized tomography or for MRI imaging. Furthermore, the method can preferably be used when the object is at least part of a jaw of a subject, in which case the registration device is adapted to fit in a reproducible position in the at least part of the jaw.

In accordance with yet another preferred embodiment of the present invention, there is provided a method for correlating positional data relating to an object, obtained by means of a tracking system, with a scanned image of the object, comprising the steps of (a) producing a scanned image of the object in the presence of a registration device having markers which are visible in the scanned image, the markers being located in fixed positions in the registration device, (b) locating the registration device at a position remote from the object, and determining the position such that the location of the markers is known to the tracking system, (c) obtaining positional data relating to the object by means of the tracking system, and (d) adjusting the relationship between the scanned image of the object and the positional data of the object such that the position of the markers on the scanned image coincides with the location of the markers known to the tracking system.

In accordance with still another preferred embodiment of the present invention, in the above-mentioned method, the step of determining the position may be preferably performed either using a manually directed position sensing device, or by inserting the registration device into a registration jig which accommodates the registration device in a known position, and recording the position of the jig with the tracking system.

The above-described method can be preferably used for computerized tomography or for MRI imaging. Furthermore, the method can preferably be used when the object is at least part of a jaw of a subject. If the object is at least part of a jaw of a subject, the registration device is preferably adapted to fit in a reproducible position in the at least part of the jaw of the subject.

In accordance with a further preferred embodiment of the present invention, for dental use, the registration device may be split into parts, such that only part of the registration device need be in the mouth of the subject during treatment. In such a case, the part of the registration device in the mouth of the subject during treatment is preferably adapted such that it does not interfere with the progress of the dental treatment. In the above methods, the registration jig is preferably located remote from the subject.

Furthermore, in accordance with yet another preferred embodiment of the present invention, in the above-mentioned method in which the registration device is adapted to fit in a reproducible position in the at least part of the jaw of the subject the step of obtaining positional data about the at least part of a jaw of a subject may preferably be performed by providing the registration device with trackability by the tracking system, and may also comprise the additional steps of: (a) juxtaposing the registration device in a reproducible manner with at least one tooth of the subject, (b) tracking the position of the registration device, and (c) compensating the positional data of the at least part of a jaw of a subject according to the tracked position of the registration device, such that the relationship between the scanned image of the object and the positional data of the object is maintained during movement of the subject. In this method, the step of providing the registration device with trackability by the tracking system may be performed by attaching to the registration device a body adapted to be tracked by the tracking system. Furthermore, the method may comprise the additional step of providing a drill with trackability by the tracking system, such that the position of the drill in relation to the at least one tooth of the subject can be determined.

There is even further provided in accordance with another preferred embodiment of the present invention a registration device for positional determination of at least part of a jaw of a subject, comprising (a) a portion incorporating markers, identifiable by an imaging method, and (b) a trackable position sensor, associated with the registration device, for determining the three-dimensional position of the registration device, wherein the registration device is demountable into at least two component parts for mounting in the at least part of a jaw of a subject. Preferably, the component parts are adapted to be sufficiently small that they do not interfere with a procedure to be performed in the oral cavity of the subject. Furthermore, the portion incorporating markers may preferably be demountable from the registration device, and at least one of the component parts may preferably comprise a splint adapted to conform to a shape within the oral cavity of the subject.

Furthermore, in accordance with yet another preferred embodiment of the present invention, there is provided a method for correlating positional data relating to an object, obtained by means of a tracking system, with a scanned image of the object, comprising the steps of:

(a) providing a registration device having markers, visible in the scanned image, located in known positions, and also having a reference tracking body located in a known position relative to the registration device, the position of the reference tracking body being tracked by the tracking system, (b) producing a scanned image of the object in the presence of the registration device, such that the markers are visible in the image, (c) determining the position of the registration device with the tracking system, such that the location of the markers is known to the tracking system, (d) obtaining positional data relating to the object by means of a known positional relationship between the registration device and the object, and (e) adjusting the relationship between the scanned image of the object and the positional data of the object such that the position of the markers on the scanned image coincides with the location of the markers known to the tracking system.

In the last-described method, the reference tracking body may be the registration device itself. Furthermore, the object may be at least part of a jaw of a subject. Finally, the scanned image may preferably be a CT image or an MRI image.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
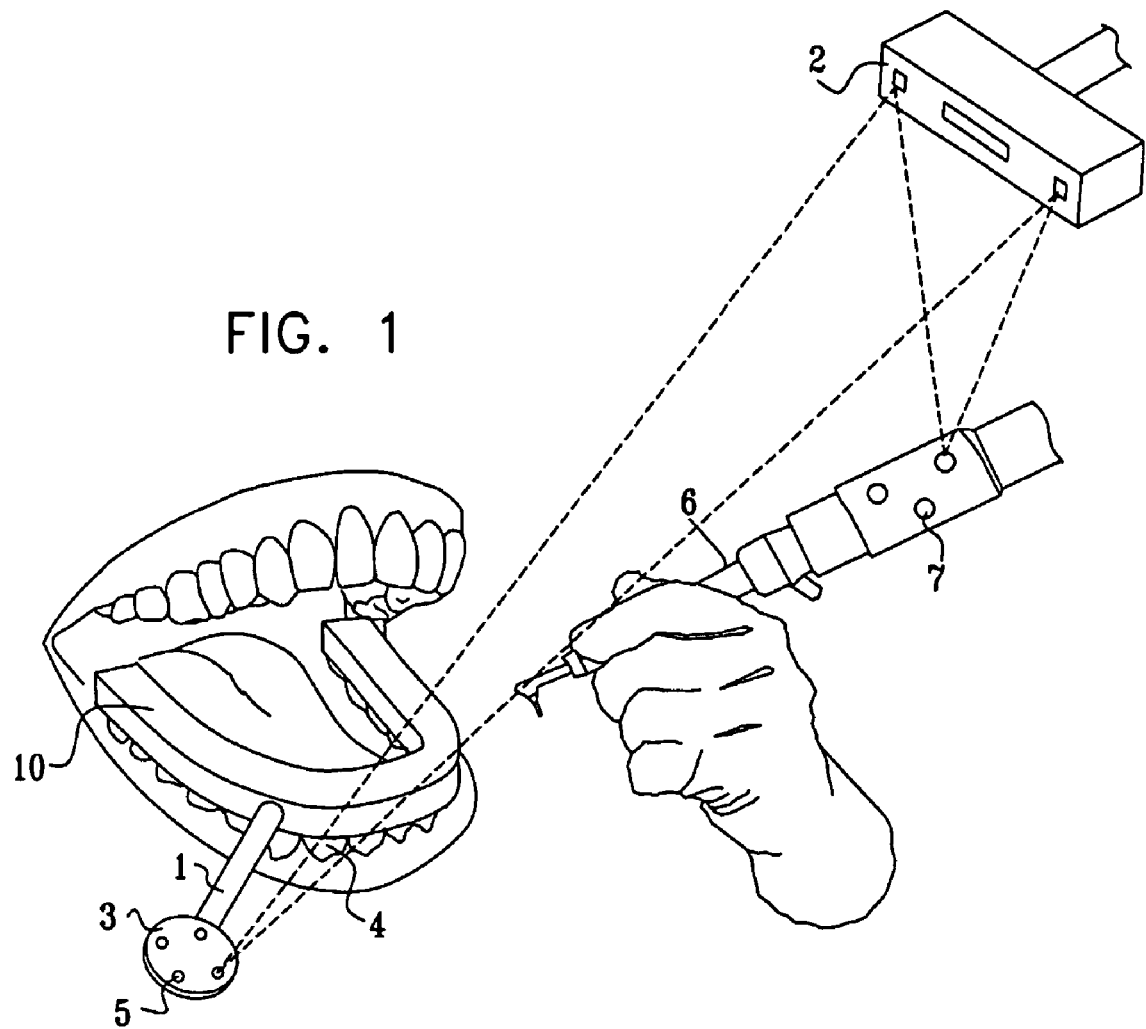
FIG. 1 is a schematic illustration of parts of a system for performing image guided implantology, to illustrate the utilization of preferred methods and devices of the present invention.

Reference is now made to FIG. 1, which illustrates schematically some of the parts of a system for performing image guided implantology, to illustrate the utilization of preferred methods and devices of the present invention. The teeth of the lower jaw 4 of a patient are shown, with a registration device 10 preferably having a horseshoe shape and adapted so that it sits comfortably in the mouth of the subject in a defined position relative to the subject's teeth. For clarity, the jaw is shown open in FIG. 1, but during the scanning process, the mouth would generally be closed to grip the registration device. Furthermore, although the complete registration device is shown in FIG. 1, in practice, when tracking is needed during a dental procedure, only part of the registration device would be left in the patient's mouth, to provide clear access to the tooth to be worked on, as explained hereinbelow. To the registration device is preferably attached, by means of a connection rod 1, a reference tracking body 3, in which are positioned a number of LED emitters 5. The light from these LED's is tracked by means of the sensor head 2 of a three-dimensional tracking system, thus enabling movement of the patient during the dental procedure to be followed by the tracking system. A specially adapted dental drill 6 is preferably used with the system. The drill body or shank is preferably equipped with a number of LED emitters 7, whose radiation too is tracked by means of the sensor head 2 of the three-dimensional tracking system, thus enabling movement of the drill during the dental procedure to be followed by the tracking system.

Figure 2:
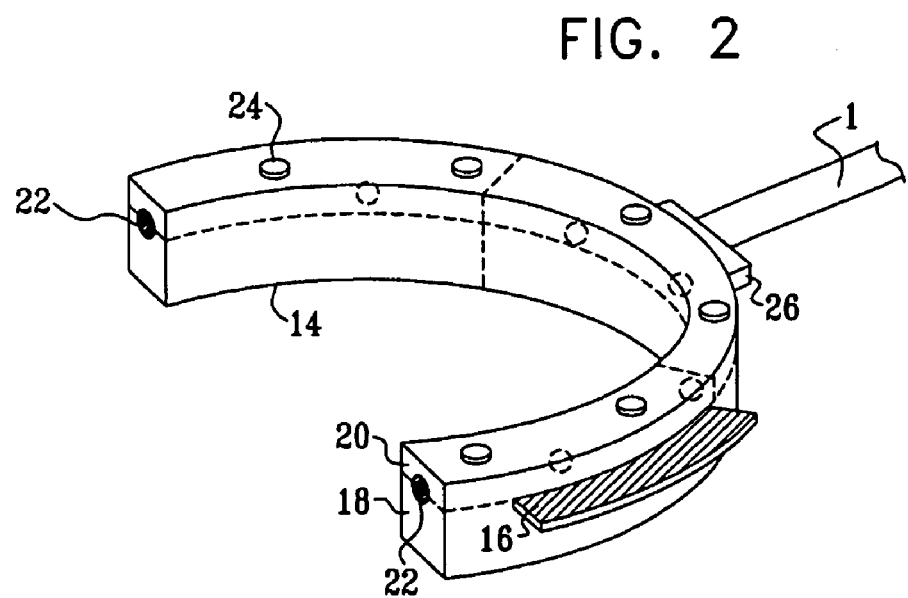
FIG. 2 is a close-up schematic illustration of the horseshoe-shaped registration device of FIG. 1, used in preferred embodiments of the methods according to the present invention.

Reference is now made to FIG. 2, which is a closer schematic illustration of the registration device 10 of FIG. 1. The accurate location of the registration device relative to the patient's teeth can preferably be achieved by constructing the contact surface of the registration device 14, or of a splint part 16 of the registration device, to fit the contour of the subject's teeth, as is well known in the dental arts. Such a splint part is typically constructed of a flexible but hardenable material which is allowed to conform to the shape of the tooth or teeth before being hardened. The registration device is preferably made of a plastic material and is manufactured of a body part 18, and a cover part 20. In the cover part are located a number of balls 22 in predefined positions, constructed of a material which appears clearly on the CT images. Metallic balls are particularly suitable. The registration device has a number of mechanical protuberances or indentations 24 around its body, such that it can be interfaced in a predefined and stable manner with other devices, such as a registration jig, as will be explained hereinbelow. The registration device 10 also has a screwed attachment point 26, to which can be attached a removable rod 1 which supports accessories necessary for performing preferred methods of the present invention, as will be explained hereinbelow. The registration device is preferably constructed of three parts, a center anterior part, a posterior left part and a posterior right part. During surgery on the teeth, those parts which would interfere with the work of the dental surgeon are removed, and the registration device is held in the mouth of the subject by the remaining part. Most preferably, the registration device is held in the mouth by means of a splint 16, attached adhesively to the teeth of the patient by methods known in the dental arts. The splint 16 may preferably be located in the posterior right part of the registration device, as shown in FIG. 2, or in the center anterior part, or in the posterior left part.

Figure 3:
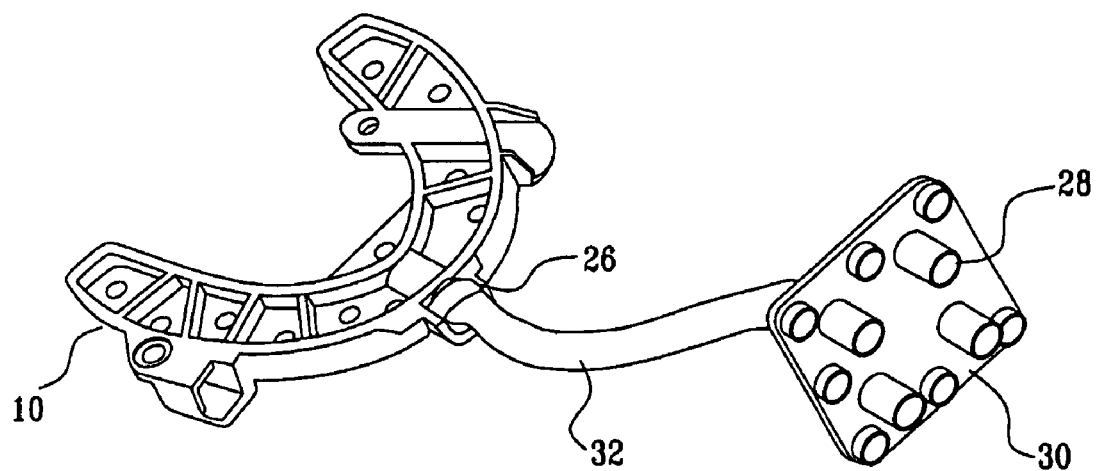
FIG. 3 is a schematic illustration of the horseshoe registration device of FIG. 1, with a distortion body attached to it, to enable a method of compensation of distortions in a CT scan of a patient's jaw.

Reference is now made to FIG. 3, which is a schematic illustration of the horseshoe-shaped registration device 10 according to a preferred embodiment of the present invention, such as that shown in FIGS. 1 and 2. The registration device has a distortion body 30 attached to it by means of a connector rod 32 screwed into the attachment point 26. This distortion body is used, according to a preferred method of the present invention, to allow compensation of distortions in the CT scan of the patient's jaw. The distortion body contains fiducial markers 28, like the balls used in the registration device itself, and made of a material that is accurately identified in a scanned CT image. The fiducial markers are disposed in a predetermined three-dimensional pattern which provides good spatial and angular discrimination when imaged in a CT scan. The distortion body preferably includes placement of markers in a plane perpendicular to the general plane of the registration device itself, which is approximately in the plane of the teeth. This is an important feature since the imaging process usually used in CT jaw imaging scans in slices generally parallel to the planes of the teeth, and the nature of the distortions present in CT images is such that it is important to correct for distortion generated perpendicular to the scanning planes. This is why the fiducial markers in the registration body itself are not generally used for correcting CT image distortion, as they would give less accurate correction than using those in the distortion body.

Figure 4:
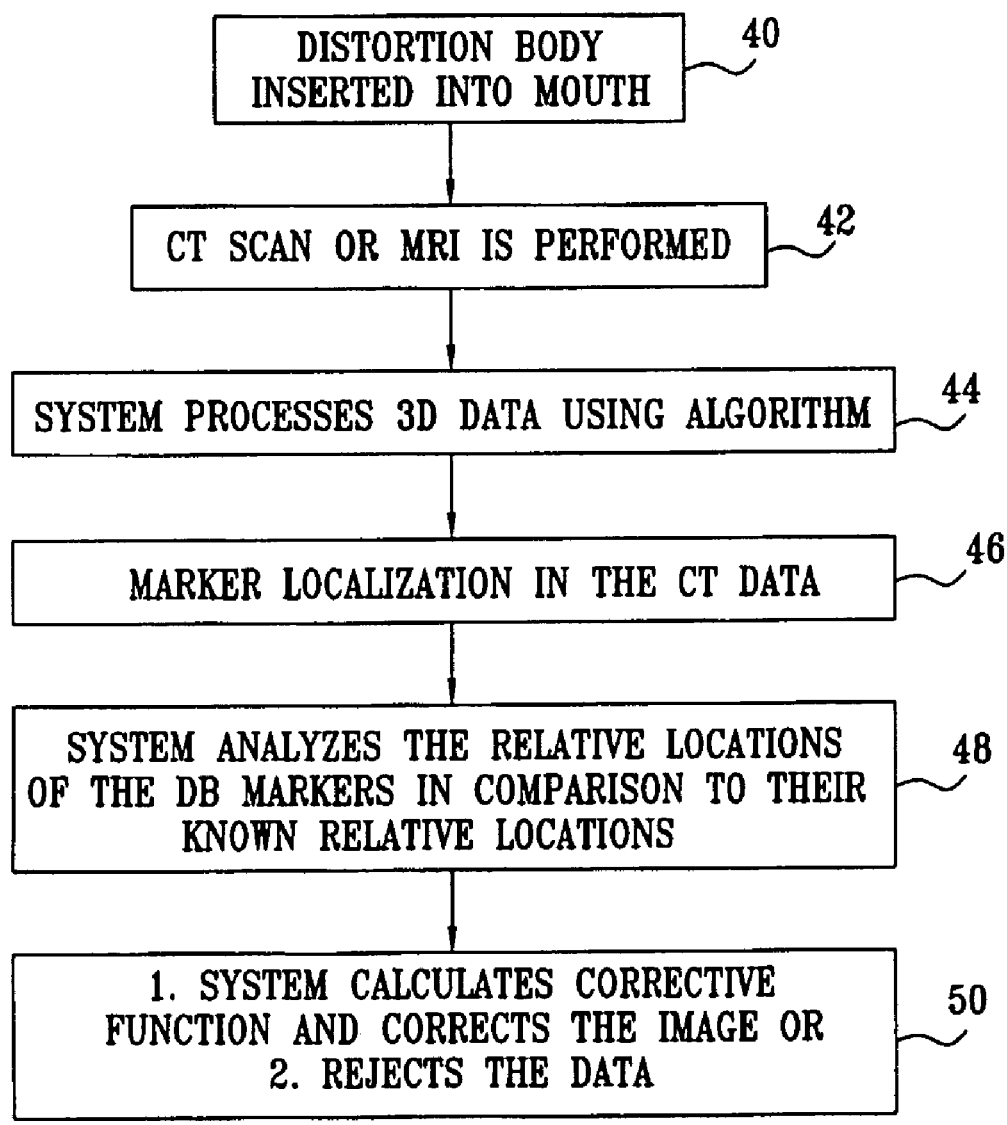
FIG. 4 is a block diagram of a method, according to a preferred embodiment of the present invention, suitable for using the distortion body to correct distortions in a CT scan of the patient's mouth.

Reference is now made to FIG. 4 which is a block diagram of a method, according to a preferred embodiment of the present invention, suitable for using the distortion body to correct distortions in a CT or MRI scan of the patient's mouth. According to this preferred method, at step 40, the horseshoe registration device with the distortion body 30 attached to it is inserted into the patient's mouth, and is firmly located in its correct position. In step 42, a three-dimensional CT or MRI scan of the patient's jaw is then performed. In step 44, an algorithm is used to process the three-dimensional data obtained from the CT or MRI scan in step 42. In step 46, the relative positions of the fiducial markers in the CT or MRI scan is calculated. These calculated positions are obtained inclusive of any distortions generated by the CT or MRI scanning system. In step 48, these calculated distorted positions are compared with the known true relative positions of the markers, and in step 50, based on this comparison, either the data of that scan is rejected since the image distortion is greater than a predetermined permissible amount, or a correction function is generated therefrom which is used to correct the distortion in the CT or MRI images obtained.

Though the above method has been described in terms of the correction of distortions arising in a CT or MRI scan, it is to be understood that the method is not meant to be limited to CT or MRI imaging, but is equally applicable to any other suitable form of three-dimensional imaging. Throughout this application, it is to be understood that reference to CT or MRI scanning is only used as preferred examples of a three-dimensional scanning imaging process, and that the methods throughout are equally applicable to other suitable forms of imaging.

Once the CT or MRI images have been corrected by means of the above-described methods for any inherent distortions or for patient movement induced distortions, it is necessary to correlate the CT or MRI images previously obtained and stored in the system, with the information generated by the scanner in real time of the position of the dentist's drill and of the patient's teeth, both of which may be constantly changing with movement. This procedure is carried out by means of another preferred method of the present invention, which is illustrated in FIG. 5, which is a block diagram of the steps of the method.

Figure 5:
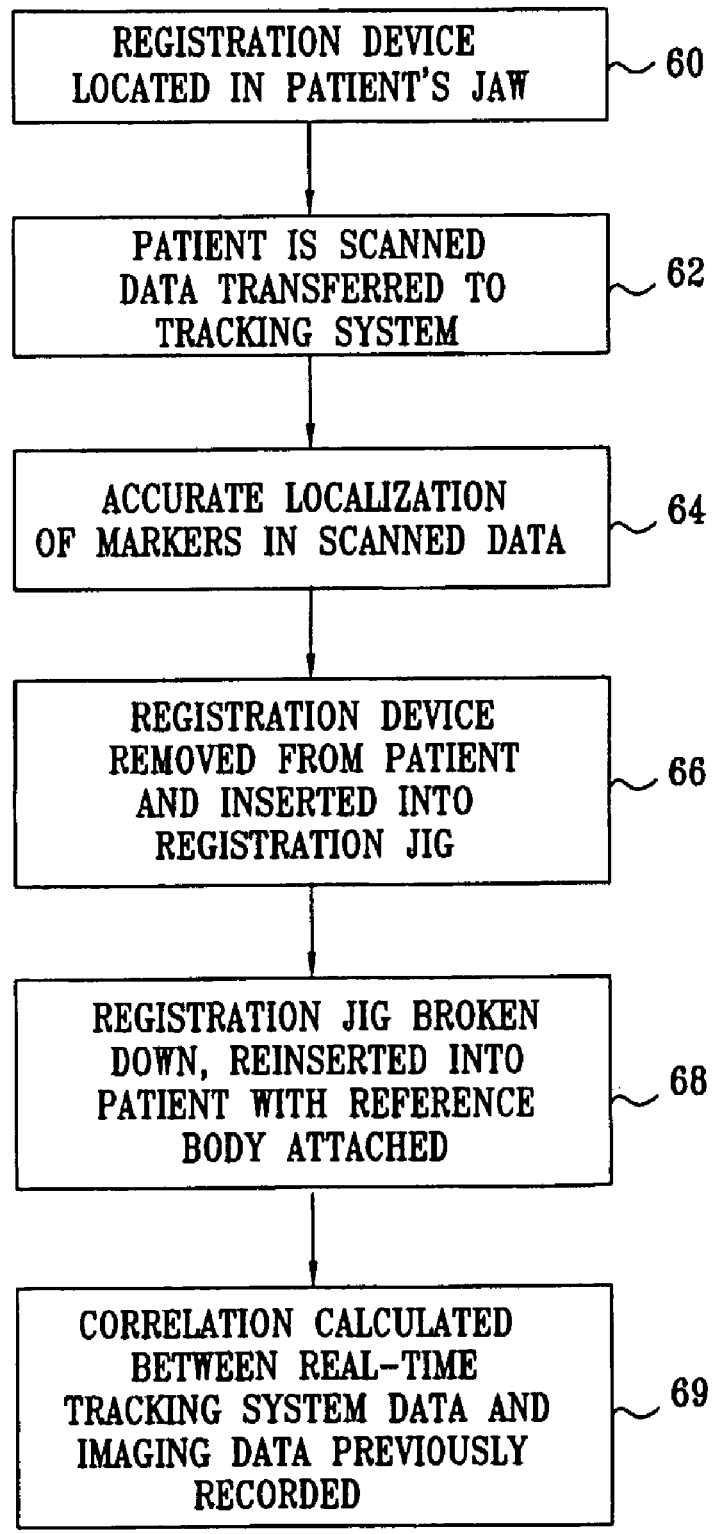
FIG. 5 is a block diagram of the steps of a method, according to a preferred embodiment of the present invention, suitable for correlating CT images previously obtained, with spatial information generated in real time by the scanner of the position of the dentist's drill and the patient's teeth.

In step 60 of FIG. 5, the whole registration device 10 complete with its marker balls, as described above, is located in a defined position in the jaw of the patient. In step 62, the patient is scanned, preferably by a CT or MRI imaging system, and the data is transferred to the tracking system as the base image display to be used by the dental surgeon in performing the procedure to be undertaken. This image data is later to be correlated by the system with positional data obtained by the tracking system. Since during the scanning step, the fiducial markers are located within the registration device, their position relative to the patient's teeth is thus defined in the stored image data. In step 64, the scanned data is processed by the system, and the three-dimensional data is utilized to derive an accurate localization of the markers' positions, and hence also the position of the registration device within the scanned data.

So far, the system has stored scanned images of the patient's mouth, including information relating to the position of the markers, but without any relation to the real world of the patient's jaw and the surgeon's drill, as viewed by the real-time tracking system. This bridging step between the virtual world of the scanned image data and the real tracked world of the dental surgery is achieved by means of a registration process, in which the position of the registration device is tracked independently of the patient. According to the preferred method illustrated in FIG. 5, this registration process is accomplished by mounting the registration device in a special registration jig. In step 66 of FIG. 5, transfer of the registration device to this registration jig is shown as being performed after being imaged within the patient's mouth, but the registration process, according to this preferred embodiment of the present invention, may be performed before or after imaging of the registration device in the patient's mouth.

Figure 6:
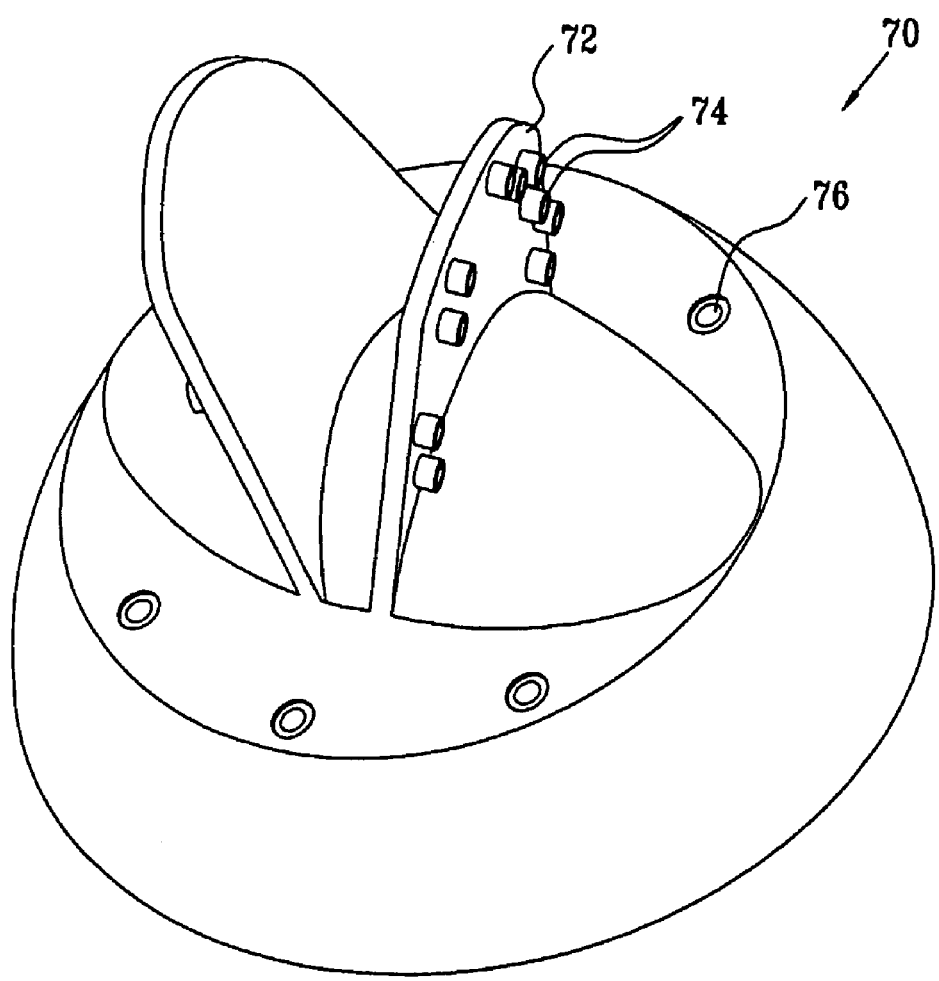
FIG. 6 is a schematic drawing of a registration jig constructed and operative according to a preferred embodiment of the present invention, utilized for executing the method described in the block diagram of FIG. 5.

Reference is now made to FIG. 6, which is a schematic drawing of a registration jig 70, constructed and operative according to a preferred embodiment of the present invention. The registration jig has a reference surface 72, onto which the horseshoe shaped registration device 10 can be affixed in a repeatable and defined manner. The accuracy of location of the registration device within the registration jig is ensured preferably by means of an array of pins 74, which interface with the indentations 24 in the surface of the horseshoe shaped registration device 10, as shown in FIG. 2. Alternatively and preferably, if the horseshoe shaped registration device 10 is provided with locating pins, the registration jig would be provided with matching indentations.

In the top surface of the registration jig are fitted a number of LED's 76, which act as markers for the registration jig position as recorded by the tracking system. When the registration jig is positioned in the field of view of the tracking system sensor head 2 (shown in FIG. 1), the emitted radiation from these LED's is identified and measured by the tracking system 2, thereby defining the position of the registration jig 70. Since the registration device 10 is attached to the registration jig in a manner that ensures an accurate and reproducible spatial relationship between the fiducial markers in the registration device and the LED markers 76 in the registration jig, the tracking system thus also enables the spatial position of the fiducial markers in the registration device, and hence the registration device itself, to be accurately related to the reference co-ordinates of the tracking system. The position of the registration device could also preferably be determined by the use of a manual digitizing stylus, such as is touched by the operator onto specific points to be co-ordinatized, and the co-ordinates entered at those points by manually pressing an enter-key on the stylus. However, the use of the registration jig provides a more convenient method of position registration, which is less dependent on operator skill, and thus more reliable. The use of a registration method outside of the mouth of the patient, regardless of the specific method used, is an advantage over prior art registration methods, since the registration can be simply performed by a technician, and not the dental surgeon himself.

Referring now back to the block diagram of FIG. 5, in step 68 of the method of image correlation according to the present invention, the cover of the registration device 10 is removed and the fiducial markers taken out, so that the body will fit comfortably into the patient's mouth. Furthermore, the registration device body may be broken down into its parts, and use is preferably made only of that part which will give the dental surgeon easy access to the teeth on which he is to work. To that part is attached a reference tracking body 8, such as that shown in the embodiment of FIG. 1. FIG. 1 differs from the presently described step only in that in FIG. 1, the whole of the registration device 10 is shown in order to illustrate the complete structure of the registration device. Once the reference tracking body 3 has been affixed to it, the operative part of the registration device is inserted in its correct position in the patient's mouth, and is preferably attached to the patient's teeth by means of an associated splint, as explained hereinabove, and the dental surgeon can begin the planned procedure. The tracking system detects the radiation emitted by the LED markers 5 on the reference tracking body 3 and thus is able to define the position of the registration device 10, and hence the real-world position of the patient's teeth in the system, and hence also on the monitor used by the dental surgeon. By using the above-described preferred method of this embodiment of the present invention, whereby the tracking system is able to relate to the position of the teeth on the scanned images by means of the known position of the fiducial markers present when the images were produced, the system is thus also able to correlate the previously acquired images with the actual real-time position of the patient's teeth, as shown in step 69 of FIG. 5, and to display the images on the monitor in the true position of the patient's actual teeth. Movements of the patient during surgery are followed by the tracking system, and the monitor image corrected accordingly. The drill position, which is also tracked in real time by means of LED markers 7 on its shank, can thus be displayed overlaid onto the images on the monitor of the patient's teeth, with great accuracy, both spatially and angularly, and without fear of inaccuracy due to patient movement.

According to another preferred embodiment of the present invention, the registration process can be performed by directly determining the position of the registration device, and hence the position of its associated fiducial markers, by means of the reference tracking body attached to the registration device. The reference tracking body, shown as item 3 in FIG. 1, has hitherto been disclosed only as being used for tracking motion of the patient during the dental procedure. Consequently, in the prior art, and in the hitherto described embodiments of the present invention, it is shown as being of a lightweight construction, in order not to be unduly burdensome on the patient. Since its function is to track relative motion of the patient's jaw during the course of a single treatment, it need not be attached to the registration device in a reproducible and repeatable manner, and the connection can be light and not unduly rigid. In order to use it in the registration process, however, the position of the reference tracking body relative to the registration device must be definitively fixed, so that the registration process can be meaningfully performed. This may involve a sturdier connection means than that shown in FIG. 1, which may prove to be uncomfortable for the patient. However, the use of a lightweight but repeatable and rigid fixing method for attaching the reference tracking body to the registration device would make a separate registration procedure superfluous, by means of direct referencing of the position of the fiducial markers to the tracked position of the reference tracking body. In effect, the referencing procedure is performed once only during the manufacturing process of the registration device and the reference tracking body, whereby they are given a predefined and fixed mutual disposition. According to this preferred embodiment of the present invention, the reference tracking body need not then be a separate rigidly attached part, but could be built into or onto the registration device, such that the reference tracking body can be considered to be an integral part of the registration device, or vice versa.

Though the above mentioned preferred embodiments of the present invention have been described in terms of the correlation of previously obtained CT or MRI imaging to the real-life situation for the performance of image-guided implantation preparation by a dental surgeon, it is to be understood that the invention is not meant to be limited to this application. The methods and apparatus described hereinabove are equally applicable to other fields of medical or industrial real time processing on a subject previously imaged by a system unrelated to that used to perform the process.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

I claim:

1. A method of compensating for distortions generated in an imaging process, comprising the steps of:

providing a registration device with a plurality of markers disposed in a predetermined three-dimensional pattern, said markers being rendered visible in said imaging process;

producing a scanned image of an object of interest in the presence of said registration device; and correcting the data of said scanned image such that the image of said markers accurately reproduces said predetermined three-dimensional pattern.

2. The method according to claim 1 wherein said plurality of markers are disposed within said registration device.

3. The method according to claim 1 wherein said plurality of markers are disposed within a body attached to said registration device.

4. The method according to claim 1 wherein said imaging process is selected from a group consisting of computerized tomography and an MRI process.

5. The method according to claim 1 wherein said object is at least part of a jaw of a subject.

6. The method according to claim 5 wherein said registration device is adapted to fit in a reproducible position in said at least part of said jaw.

7. A method for correlating positional data relating to an object, obtained by means of a tracking system, with a scanned image of said object, comprising the steps of:

producing a scanned image of said object in the presence of a registration device having markers which are visible in said scanned image, said markers being located in fixed positions in said registration device;

relocating said registration device to a position remote from said object and causing said tracking system to track said markers of said registration device and thus ascertain said position;

obtaining positional data relating to said object by means of said tracking system; and adjusting the relationship between said scanned image of said object and said positional data of said object such that the position of said markers on said scanned image coincides with the location of said markers known to said tracking system.

8. The method according to claim 7 wherein said causing said tracking system comprises using a manually directed position sensing device.

9. The method according to claim 7 wherein said causing said tracking system comprises inserting said registration device into a registration jig which accommodates said registration device in a known position, and recording the position of said jig with said tracking system.

10. The method according to claim 7 wherein said object is at least part of a jaw of a subject.

11. The method according to claim 7 wherein said scanned image is selected from a group consisting of a CT image and an MRI image.

12. The method according to claim 10 wherein said registration device is adapted to fit in a reproducible position in said at least part of a jaw of said subject.

13. The method according to claim 12 wherein said registration device is split into parts, such that only part of said registration device need be in the mouth of said subject during dental treatment.

14. The method according to claim 13 wherein said part of said registration device in the mouth of said subject during dental treatment is adapted such that it does not interfere with the progress of said dental treatment.

15. The method according to claim 9 wherein said registration jig is located remote from said object.

16. The method according to claim 12, and wherein said step of obtaining positional data comprises providing said registration device with trackability by said tracking system, and said method also comprises the steps of:

juxtaposing said registration device in a reproducible manner with at least one tooth of said subject;

tracking the position of said registration device; and compensating said positional data of said at least part of a jaw of a subject according to the tracked position of said registration device, such that said relationship between said scanned image of said object and said positional data of said object is maintained during movement of said subject.

17. The method according to claim 16, and wherein said step of providing said registration device with trackability by said tracking system is performed by attaching to said registration device a body adapted to be tracked by said tracking system.

18. The method according to claim 16, and also comprising the step of providing a drill with trackability by said tracking system, such that the position of said drill in relation to said at least one tooth of said subject can be determined.

19. A method for correlating positional data relating to an object, obtained by means of a tracking system, with a scanned image of said object, comprising the steps of:

providing a registration device having markers, visible in said scanned image, located in known positions, and also having a reference tracking body located in a known position relative to said registration device, the position of said reference tracking body being tracked by said tracking system;

producing a scanned image of said object in the presence of said registration device, such that said markers are visible in said image;

determining the position of said registration device with said tracking system, such that the location of said markers is known to said tracking system;

obtaining positional data relating to said object by means of a known positional relationship between said registration device and said object; and ascertaining whether distortions exist between said scanned image of said object and said positional data of said object wherein the position of said markers on said scanned image do not coincide with the location of said markers known to said tracking system.

20. The method according to claim 19, and wherein said reference tracking body is part of said registration device itself.

21. The method according to claim 19, and wherein said object is at least part of a jaw of a subject.

22. The method according to claim 20, and wherein said object is at least part of a jaw of a subject.

23. The method according to claim 19, and wherein said scanned image is selected from a group consisting of a CT image and an MRI image.

24. The method according to claim 20, and wherein said scanned image is selected from a group consisting of a CT image and an MRI image.

* * * * *